(12) United States Patent
Vidal et al.

(10) Patent No.: US 7,524,815 B2
(45) Date of Patent: Apr. 28, 2009

(54) OSTEOPROTEGERIN IN MILK

(75) Inventors: Karine Vidal, Lausanne (CH); Peter Van Den Broek, WJ Maarn (NL); Elizabeth Offord Cavin, Poliez-Pittet (CH); Anne Donnet-Hughes, Saint-Legier (CH)

(73) Assignee: Nestec S.A., Vevey (CH)

( * ) Notice: Subject to any disclaimer, the term of this patent is extended or adjusted under 35 U.S.C. 154(b) by 0 days.

(21) Appl. No.: 11/144,236

(22) Filed: Jun. 2, 2005

(65) Prior Publication Data

US 2005/0288219 A1 Dec. 29, 2005

Related U.S. Application Data

(60) Division of application No. 10/676,358, filed on Oct. 2, 2003, which is a continuation of application No. PCT/EP02/02912, filed on Mar. 15, 2002.

(30) Foreign Application Priority Data

Apr. 3, 2001 (EP) .................. 01108414

(51) Int. Cl.
*A61K 38/17* (2006.01)
(52) U.S. Cl. ................ 514/8; 514/2; 514/12; 530/350; 424/9.1; 435/69.1; 426/656
(58) Field of Classification Search ........... 514/2, 514/8, 12; 530/350; 435/69.1; 426/656; 424/9.1
See application file for complete search history.

(56) References Cited

U.S. PATENT DOCUMENTS

| 4,946,701 | A | 8/1990 | Tsai et al. |
|---|---|---|---|
| 5,182,926 | A | 2/1993 | Carns et al. |
| 5,897,903 | A | 4/1999 | Gerhard-Rieben et al. |
| 5,997,929 | A | 12/1999 | Heeb et al. |
| 6,015,938 | A * | 1/2000 | Boyle et al. ........... 800/18 |
| 6,093,436 | A | 7/2000 | Zheng et al. |
| 6,149,957 | A | 11/2000 | Mandralis et al. |
| 6,413,558 | B1 | 7/2002 | Weber et al. |
| 6,855,808 | B2 * | 2/2005 | Goto et al. ........... 530/350 |
| 6,919,312 | B2 * | 7/2005 | Mochizuki et al. ........ 514/12 |

FOREIGN PATENT DOCUMENTS

| DE | 3821374 | 1/1990 |
|---|---|---|
| EP | 0826308 | 8/1996 |
| EP | 0916267 | 9/1998 |
| EP | 0934702 | 1/1999 |
| FR | 2039157 | 4/1970 |
| GB | 124309 | 3/1919 |
| GB | 2285578 | 7/1995 |
| JP | 2000102362 | * 4/2000 |
| WO | WO99/52378 | 10/1999 |
| WO | WO99/61038 | 12/1999 |
| WO | WO00/44238 | 8/2000 |

OTHER PUBLICATIONS

Simonet et al. , Cell 89, 309-319 (1997).*

* cited by examiner

*Primary Examiner*—Chih-Min Kam
(74) *Attorney, Agent, or Firm*—K&L Gates LLP

(57) ABSTRACT

The present invention pertains to osteoprotegerin obtainable from milk sources, in particular human and bovine milk. The present invention also relates to the use thereof for preparing an ingestible preparation and/or a pharmaceutical composition, in particular to the use of such a preparation/composition for preventing or treating disorders associated with bone metabolism and immune function.

4 Claims, 8 Drawing Sheets

```
MKLATAFTILTAVLAAPLAAPAPAPDAAPAAVPEGPAAAAYSSILSVVAKQSKKFKHHKR
DLDEKDQFIVVFDSSATVDQIASEIQKLDSLVDEDSSNGITSALDLPVYTDGSGFLGFVG
KFNSTIVDKLKESSVLTVEPDTIVSLPEIPASSAAKRETFPPKYLHYDEETSHQLLCDKC
PPGTYLKQHCTAKWKTVCAPCPDHYYTDSWHTSDECLYCSPVCKELQYVKQECNRTHNRV
CECKEGRYLEIEFCLKHRSCPPGFGVVQAGTPERNTVCKRCPDGFFSNETSSKAPCRKHT
NCSVFGLLLTQKGNATHDNICSGNSESTQKCGIDVTLCEEAFFRFAVPTKFTPNWLSVLV
DNLPGTKVNAESVERIKRQHSSQEQTFQLLKLWKHQNKAQDIVKKIIQDIDLCENSVQRH
IGHANLTFEQLRSLMESLPGKKVGAEDIEKTIKACKPSDQILKLLSLWRIKNGDQDTLKG
LMHALKHSKTYHFPKTVTQSLKKTIRFLHSFTMYKLYQKLFLEMIGNQVQSVKISCL
```

Figure 6

```
  1  TCCGGCCTCTTCGGCCgccaagcgaGAAACGTTTCCTCCAAAGTACCTTCATTATGACGA   60
  1           xpr2            E  T  F  P  P  K  Y  L  H  Y  D  E   12

61  AGAAACCTCTCATCAGCTGTTGTGTGACAAATGTCCTCCTGGTACCTACCTAAAACAACA  120
 13   E  T  S  H  Q  L  L  C  D  K  C  P  P  G  T  Y  L  K  Q  H   32

121  CTGTACAGCAAAGTGGAAGACCGTGTGCGCCCCTTGCCCTGACCACTACTACACAGACAG  180
 33   C  T  A  K  W  K  T  V  C  A  P  C  P  D  H  Y  Y  T  D  S   52

181  CTGGCACACCAGTGACGAGTGTCTATACTGCAGCCCCGTGTGCAAGGAGCTGCAGTACGT  240
 53   W  H  T  S  D  E  C  L  Y  C  S  P  V  C  K  E  L  Q  Y  V   72

241  CAAGCAGGAGTGCAATCGCACCCACAACCGCGTGTGCGAATGCAAGGAAGGGCGCTACCT  300
 73   K  Q  E  C  N  R  T  H  N  R  V  C  E  C  K  E  G  R  Y  L   92

301  TGAGATAGAGTTCTGCTTGAAACATAGGAGCTGCCCTCCTGGATTTGGAGTGGTGCAAGC  360
 93   E  I  E  F  C  L  K  H  R  S  C  P  P  G  F  G  V  V  Q  A  112

361  TGGAACCCCAGAGCGAAATACAGTTTGCAAAAGATGTCCAGATGGGTTCTTCTCAAATGA  420
113   G  T  P  E  R  N  T  V  C  K  R  C  P  D  G  F  F  S  N  E  132

421  GACGTCATCTAAAGCACCCTGTAGAAAACACACAAATTGCAGTGTCTTTGGTCTCCTGCT  480
133   T  S  S  K  A  P  C  R  K  H  T  N  C  S  V  F  G  L  L  L  152

481  AACTCAGAAAGGAAATGCAACACACGACAACATATGTTCCGGAAACAGTGAATCAACTCA  540
153   T  Q  K  G  N  A  T  H  D  N  I  C  S  G  N  S  E  S  T  Q  172

541  AAAATGTGGAATAGATGTTACCCTGTGTGAGGAGGCATTCTTCAGGTTTGCTGTTCCTAC  600
173   K  C  G  I  D  V  T  L  C  E  E  A  F  F  R  F  A  V  P  T  192

601  AAAGTTTACGCCTAACTGGCTTAGTGTCTTGGTAGACAATTTGCCTGGCACCAAAGTAAA  660
193   K  F  T  P  N  W  L  S  V  L  V  D  N  L  P  G  T  K  V  N.  212

661  CGCAGAGAGTGTAGAGAGGATAAAACGGCAACACAGCTCACAAGAACAGACTTTCCAGCT  720
213   A  E  S  V  E  R  I  K  R  Q  H  S  S  Q  E  Q  T  F  Q  L  232
                                       C
721  GCTGAAGTTATGGAAACATCAAAACAAAGACCAAGATATAGTCAAGAAGATCATCCAAGA  780
233   L  K  L  W  K  H  Q  N  K  D  Q  D  I  V  K  K  I  I  Q  D  252
                                 A
781  TATTGACCTCTGTGAAAACAGCGTGCAGCGGCACATTGGACATGCTAACCTCACCTTCGA  840
253   I  D  L  C  E  N  S  V  Q  R  H  I  G  H  A  N  L  T  F  E  272

841  GCAGCTTCGTAGCTTGATGGAAAGCTTACCGGGAAAGAAAGTGGGAGCAGAAGACATTGA  900
273   Q  L  R  S  L  M  E  S  L  P  G  K  K  V  G  A  E  D  I  E  292

901  AAAAACAATAAAGGCATGCAAACCCAGTGACCAGATCCTGAAGCTGCTCAGTTTGTGGCG  960
293   K  T  I  K  A  C  K  P  S  D  Q  I  L  K  L  L  S  L  W  R  312

961  AATAAAAAATGGCGACCAAGACACCTTGAAGGGCCTAATGCACGCACTAAAGCACTCAAA 1020
313   I  K  N  G  D  Q  D  T  L  K  G  L  M  H  A  L  K  H  S  K  332
```

Figure 7A Sequence of milk OPG.

```
1021  GACGTACCACTTTCCCAAAACTGTCACTCAGAGTCTAAAGAAGACCATCAGGTTCCTTCA   1080
333    T  Y  H  F  P  K  T  V  T  Q  S  L  K  K  T  I  R  F  L  H    352

1081  CAGCTTCACAATGTACAAATTGTATCAGAAGTTATTTTTAGAAATGATAGGTAACCAGGT   1140
353    S  F  T  M  Y  K  L  Y  Q  K  L  F  L  E  M  I  G  N  Q  V    372

1141  CCAATCAGTAAAAATAAGCTGCTTATAACTAGTATCACTAGT   1182
373    Q  S  V  K  I  S  C  L                      380
```

Figure 7B Sequence of milk OPG. (Continued)

SEQUENCE LISTING

<160> NUMBER OF SEQ ID NOS: 7

<210> SEQ ID NO 1
<211> LENGTH: 380
<212> TYPE: PRT
<213> ORGANISM: homo sapiens

<400> SEQUENCE: 1

Glu Thr Phe Pro Pro Lys Tyr Leu His Tyr Asp Glu Thr Ser His
1               5                   10                  15

Gln Leu Leu Cys Asp Lys Cys Pro Pro Gly Thr Tyr Leu Lys Gln His
                20                  25                  30

Cys Thr Ala Lys Trp Lys Thr Val Cys Ala Pro Cys Pro Asp His Tyr
            35                  40                  45

Tyr Thr Asp Ser Trp His Thr Ser Asp Glu Cys Leu Tyr Cys Ser Pro
        50                  55                  60

Val Cys Lys Glu Leu Gln Tyr Val Lys Gln Glu Cys Asn Arg Thr His
65                  70                  75                  80

Asn Arg Val Cys Glu Cys Lys Glu Gly Arg Tyr Leu Glu Ile Glu Phe
                85                  90                  95

Cys Leu Lys His Arg Ser Cys Pro Pro Gly Phe Gly Val Val Gln Ala
            100                 105                 110

Gly Thr Pro Glu Arg Asn Thr Val Cys Lys Arg Cys Pro Asp Gly Phe
        115                 120                 125

Phe Ser Asn Glu Thr Ser Ser Lys Ala Pro Cys Arg Lys His Thr Asn
130                 135                 140

Cys Ser Val Phe Gly Leu Leu Leu Thr Gln Lys Gly Asn Ala Thr His
145                 150                 155                 160

Asp Asn Ile Cys Ser Gly Asn Ser Glu Ser Thr Gln Lys Cys Gly Ile
                165                 170                 175

Asp Val Thr Leu Cys Glu Glu Ala Phe Phe Arg Phe Ala Val Pro Thr
            180                 185                 190

Lys Phe Thr Pro Asn Trp Leu Ser Val Leu Val Asp Asn Leu Pro Gly
        195                 200                 205

Thr Lys Val Asn Ala Glu Ser Val Glu Arg Ile Lys Arg Gln His Ser
210                 215                 220

Ser Gln Glu Gln Thr Phe Gln Leu Leu Lys Leu Trp Lys His Gln Asn
225                 230                 235                 240

Lys Ala Gln Asp Ile Val Lys Lys Ile Ile Gln Asp Ile Asp Leu Cys
                245                 250                 255

Glu Asn Ser Val Gln Arg His Ile Gly His Ala Asn Leu Thr Phe Glu
            260                 265                 270

Gln Leu Arg Ser Leu Met Glu Ser Leu Pro Gly Lys Lys Val Gly Ala
        275                 280                 285

Glu Asp Ile Glu Lys Thr Ile Lys Ala Cys Lys Pro Ser Asp Gln Ile
290                 295                 300

Leu Lys Leu Leu Ser Leu Trp Arg Ile Lys Asn Gly Asp Gln Asp Thr
305                 310                 315                 320

Leu Lys Gly Leu Met His Ala Leu Lys His Ser Lys Thr Tyr His Phe
                325                 330                 335

Pro Lys Thr Val Thr Gln Ser Leu Lys Lys Thr Ile Arg Phe Leu His
            340                 345                 350

Ser Phe Thr Met Tyr Lys Leu Tyr Gln Lys Leu Phe Leu Glu Met Ile

```
                355                 360                 365
Gly Asn Gln Val Gln Ser Val Lys Ile Ser Cys Leu
    370                 375                 380

<210> SEQ ID NO 2
<211> LENGTH: 28
<212> TYPE: DNA
<213> ORGANISM: artificial
<220> FEATURE:
<223> OTHER INFORMATION: PCR primer

<400> SEQUENCE: 2
actagttata agcagcttat ttttactg                                    28

<210> SEQ ID NO 3
<211> LENGTH: 23
<212> TYPE: DNA
<213> ORGANISM: artificial
<220> FEATURE:
<223> OTHER INFORMATION: PCR primer

<400> SEQUENCE: 3
ggaggcattc ttcaggtttg ctg                                         23

<210> SEQ ID NO 4
<211> LENGTH: 46
<212> TYPE: DNA
<213> ORGANISM: artificial
<220> FEATURE:
<223> OTHER INFORMATION: PCR primer

<400> SEQUENCE: 4
ccggcctctt cggccgccaa gcgagaaacg tttcctccaa agtacc                46

<210> SEQ ID NO 5
<211> LENGTH: 28
<212> TYPE: DNA
<213> ORGANISM: artificial
<220> FEATURE:
<223> OTHER INFORMATION: PCR primer

<400> SEQUENCE: 5
actagttata agcagcttat ttttactg                                    28

<210> SEQ ID NO 6
<211> LENGTH: 537
<212> TYPE: PRT
<213> ORGANISM: artificial
<220> FEATURE:
<223> OTHER INFORMATION: protein sequence including mature OPG

<400> SEQUENCE: 6

Met Lys Leu Ala Thr Ala Phe Thr Ile Leu Thr Ala Val Leu Ala Ala
1               5                   10                  15

Pro Leu Ala Ala Pro Ala Pro Ala Pro Asp Ala Ala Pro Ala Ala Val
            20                  25                  30

Pro Glu Gly Pro Ala Ala Ala Tyr Ser Ser Ile Leu Ser Val Val
        35                  40                  45

Ala Lys Gln Ser Lys Lys Phe Lys His His Lys Arg Asp Leu Asp Glu
    50                  55                  60

Lys Asp Gln Phe Ile Val Val Phe Asp Ser Ser Ala Thr Val Asp Gln
65                  70                  75                  80

Ile Ala Ser Glu Ile Gln Lys Leu Asp Ser Leu Val Asp Glu Asp Ser
```

```
                    85                  90                  95
Ser Asn Gly Ile Thr Ser Ala Leu Asp Leu Pro Val Tyr Thr Asp Gly
                100                 105                 110

Ser Gly Phe Leu Gly Phe Val Gly Lys Phe Asn Ser Thr Ile Val Asp
                115                 120                 125

Lys Leu Lys Glu Ser Ser Val Leu Thr Val Glu Pro Asp Thr Ile Val
                130                 135                 140

Ser Leu Pro Glu Ile Pro Ala Ser Ser Ala Ala Lys Arg Glu Thr Phe
145                 150                 155                 160

Pro Pro Lys Tyr Leu His Tyr Asp Glu Thr Ser His Gln Leu Leu
                    165                 170                 175

Cys Asp Lys Cys Pro Pro Gly Thr Tyr Leu Lys Gln His Cys Thr Ala
                180                 185                 190

Lys Trp Lys Thr Val Cys Ala Pro Cys Pro Asp His Tyr Tyr Thr Asp
                195                 200                 205

Ser Trp His Thr Ser Asp Glu Cys Leu Tyr Cys Ser Pro Val Cys Lys
                210                 215                 220

Glu Leu Gln Tyr Val Lys Gln Glu Cys Asn Arg Thr His Asn Arg Val
225                 230                 235                 240

Cys Glu Cys Lys Glu Gly Arg Tyr Leu Glu Ile Glu Phe Cys Leu Lys
                245                 250                 255

His Arg Ser Cys Pro Pro Gly Phe Gly Val Val Gln Ala Gly Thr Pro
                260                 265                 270

Glu Arg Asn Thr Val Cys Lys Arg Cys Pro Asp Gly Phe Phe Ser Asn
                275                 280                 285

Glu Thr Ser Ser Lys Ala Pro Cys Arg Lys His Thr Asn Cys Ser Val
                290                 295                 300

Phe Gly Leu Leu Leu Thr Gln Lys Gly Asn Ala Thr His Asp Asn Ile
305                 310                 315                 320

Cys Ser Gly Asn Ser Glu Ser Thr Gln Lys Cys Gly Ile Asp Val Thr
                325                 330                 335

Leu Cys Glu Glu Ala Phe Phe Arg Phe Ala Val Pro Thr Lys Phe Thr
                340                 345                 350

Pro Asn Trp Leu Ser Val Leu Val Asp Asn Leu Pro Gly Thr Lys Val
                355                 360                 365

Asn Ala Glu Ser Val Glu Arg Ile Lys Arg Gln His Ser Ser Gln Glu
                370                 375                 380

Gln Thr Phe Gln Leu Leu Lys Leu Trp Lys His Gln Asn Lys Ala Gln
385                 390                 395                 400

Asp Ile Val Lys Lys Ile Ile Gln Asp Ile Asp Leu Cys Glu Asn Ser
                405                 410                 415

Val Gln Arg His Ile Gly His Ala Asn Leu Thr Phe Glu Gln Leu Arg
                420                 425                 430

Ser Leu Met Glu Ser Leu Pro Gly Lys Lys Val Gly Ala Glu Asp Ile
                435                 440                 445

Glu Lys Thr Ile Lys Ala Cys Lys Pro Ser Asp Gln Ile Leu Lys Leu
                450                 455                 460

Leu Ser Leu Trp Arg Ile Lys Asn Gly Asp Gln Asp Thr Leu Lys Gly
465                 470                 475                 480

Leu Met His Ala Leu Lys His Ser Lys Thr Tyr His Phe Pro Lys Thr
                485                 490                 495

Val Thr Gln Ser Leu Lys Lys Thr Ile Arg Phe Leu His Ser Phe Thr
                500                 505                 510
```

```
Met Tyr Lys Leu Tyr Gln Lys Leu Phe Leu Glu Met Ile Gly Asn Gln
            515                 520                 525

Val Gln Ser Val Lys Ile Ser Cys Leu
    530                 535

<210> SEQ ID NO 7
<211> LENGTH: 1182
<212> TYPE: DNA
<213> ORGANISM: homo sapiens

<400> SEQUENCE: 7
tccggcctct tcggccgcca agcgagaaac gtttcctcca aagtaccttc attatgacga       60
agaaacctct catcagctgt tgtgtgacaa atgtcctcct ggtacctacc taaaacaaca      120
ctgtacagca aagtggaaga ccgtgtgcgc cccttgccct gaccactact acacagacag      180
ctggcacacc agtgacgagt gtctatactg cagccccgtg tgcaaggagc tgcagtacgt      240
caagcaggag tgcaatcgca cccacaaccg cgtgtgcgaa tgcaaggaag ggcgctacct      300
tgagatagag ttctgcttga aacataggag ctgccctcct ggatttggag tggtgcaagc      360
tggaacccca gagcgaaata cagtttgcaa aagatgtcca gatgggttct tctcaaatga      420
gacgtcatct aaagcaccct gtagaaaaca cacaaattgc agtgtctttg gtctcctgct      480
aactcagaaa ggaaatgcaa cacacgacaa catatgttcc ggaaacagtg aatcaactca      540
aaaatgtgga atagatgtta ccctgtgtga ggaggcattc ttcaggtttg ctgttcctac      600
aaagtttacg cctaactggc ttagtgtctt ggtagacaat ttgcctggca ccaaagtaaa      660
cgcagagagt gtagagagga taaaacggca acacagctca caagaacaga ctttccagct      720
gctgaagtta tggaaacatc aaaacaaagc ccaagatata gtcaagaaga tcatccaaga      780
tattgacctc tgtgaaaaca gcgtgcagcg gcacattgga catgctaacc tcaccttcga      840
gcagcttcgt agcttgatgg aaagcttacc gggaaagaaa gtgggagcag aagacattga      900
aaaaacaata aaggcatgca aacccagtga ccagatcctg aagctgctca gtttgtggcg      960
aataaaaaat ggcgaccaag acaccttgaa gggcctaatg cacgcactaa agcactcaaa     1020
gacgtaccac tttcccaaaa ctgtcactca gagtctaaag aagaccatca ggttccttca     1080
cagcttcaca atgtacaaat tgtatcagaa gttatttta gaaatgatag gtaaccaggt     1140
ccaatcagta aaaataagct gcttataact agtatcacta gt                       1182
```

OSTEOPROTEGERIN IN MILK

CROSS-REFERENCE TO RELATED APPLICATION

This application is a divisional of pending U.S. patent application Ser. No. 10/676,358 filed Oct. 2, 2003, which is a continuation of International application PCT/EP/02/02912 filed Mar. 15, 2002, the entire contents of which is expressly incorporated herein by reference thereto.

BACKGROUND OF THE INVENTION

The present invention pertains to osteoprotegerin obtainable from milk sources, and in particular, from human or bovine milk. The present invention also relates to the use of osteoprotegerin for preparing an ingestible preparation and/or a pharmaceutical composition, in particular for use in a method for preventing or treating disorders associated with bone metabolism or immune function.

In mammals, the bones provide support for the body and consist of minerals, a matrix of collagenous and non-collagenous proteins, and a cellular component. The growth and maintenance of such components are controlled by a variety of different factors involving regulation and interaction of its component cell types, i.e., the chondrocytes which form cartilage, the osteoblasts which synthesize and deposit bone matrix, and the osteoclasts responsible for resorption of bone material.

Chondrocytes are derived from mesenchymal cells and generate an initial cartilage template required for endochondral bone formation. Osteoblasts, which promote formation of bone tissue, are derived from mesenchymal osteoprogenitor cells and are located on the surface of bones where they synthesize, transport and arrange the matrix proteins. On the other hand, osteoclasts, which are responsible for bone resorption, are derived from granulocyte-monocyte precursors present in the hematopoietic marrow. The actions of osteoclasts and osteoblasts are tightly linked e.g., during the process of osteoclast mediated resorption, the protein factors which are elaborated act as signaling molecules to initiate bone renewal by osteoblasts. Osteoblasts, in turn, may influence osteoclast function through expression of soluble or membrane bound regulators. Normal bone remodeling is therefore dependent on a definite balance between the opposing functions of bone formation and bone resorption as conveyed by each of the respective cell types.

Growth factors such as fibroblast growth factor (FGF) and transforming growth factor (TGF)-(3 are stored in the bone extracellular matrix and when secreted stimulate the local release of bone progenitor cells. Thereafter, factors such as bone morphogenetic proteins (BMPs) and parathyroid hormone (PTH) influence the development to these progenitors into osteoblasts, the bone-forming cells, whose final differentiation and function are regulated by the interaction of the cell with bone matrix proteins.

During ageing an individual is subject to a gradual loss in bone mass, a phenomenon termed uncoupling, which is deemed to result from the activity of osteoclasts exceeding that of osteoblasts. In cases where this uncoupling persists for a longer period of time, more and more of the bone's material gets destroyed/resorbed and a condition called osteoporosis results.

Apart from the age-dependent phenomenon, bone loss may also be brought about by calcium or hormonal deficiency or by conditions which result in a variety of different diseases such as osteoporosis, hypercalcemia, Paget's disease of bone, bone loss due to osteoarthritis or rheumatoid arthritis or osteomyelitis, and the like. The reduced bone density generally leads to a decreased mechanical strength and increased likelihood of fracture.

Current approaches for the treatment of osteoporosis and/or related bone disorders include the use of calcium administered to the individual in need thereof. Recently, agents involved in the stimulation and/or inhibition of bone cells, such as hormones, calcitonin, insulin-like growth factor or osteoprotegerin (OPG) have also been envisaged to be usable in treating the above disease conditions. These agents are generally prepared by recombinant means and have to be formulated/prepared in a galenic form such that the respective substance may reach the target, the bone, in an active form.

PCT publication WO 00/24771 discloses nucleic acids encoding osteoprotegerin like proteins and their use in e.g. the treatment of osteoporosis. The polypeptide is synthesized by recombinant means and then formulated to be compatible with the intended route of administration. Intravenous, intradermal, subcutaneous, oral (e.g. inhalation), transdermal (topical), transmucosal and rectal administrations can be used.

In general, it is quite time-consuming and cumbersome to find a suitable galenic form for a given substance, since the ingredients utilized for this purpose must be compatible with the active substance and must also provide sufficient protection against the different conditions in the body. However, since agents stimulating bone growth are synthesized locally—in or at the bone tissue—it is difficult to administer such a substance. Normally, capsules have to be devised which assist in passing the substance through the gastrointestinal tract without getting destroyed by the adverse environmental conditions prevailing therein. However, this route of administration also has some drawbacks since the substance has to pass the liver and be transported in body fluids before it reaches the bone. Furthermore, it often leads to a reduced amount of active biological material reaching the target tissue.

Consequently, this presents a problem as to how to provide a means of administering an active substance to an individual, whereby the substance acts in a specific target tissue in the individual. This problem now has been solved by the present invention.

SUMMARY OF THE INVENTION

The present invention relates to a composition that provides osteoprotegerin obtainable from milk. The osteoprotegerin preferably has a glycosylation pattern giving rise to a polypeptide having a molecular weight of approximately 80, 130 and 200 kDa.

The osteoprotegerin can be provided in a composition. A typical composition may be a food material, an enteral composition or a pharmaceutical composition. In these materials and compositions, osteoprotegerin is present in an amount effective to assist in formation of lymphoid tissues and regulation of immune responses in a subject that consumes the composition.

The invention also relates to a method of making a food material or an enteral or pharmaceutical composition which comprises adding therein an amount of osteoprotegerin effective to assist in formation of lymphoid tissues and regulation of immune responses in a subject that consumes the composition.

Yet another embodiment relates to the ingestible product made by that method.

Another embodiment of the invention is a method for the treatment of disorders associated with bone remodeling or for the treatment or prophylaxis of immune disorders. These methods comprise administering to a person in need of such treatment one of the ingestible compositions of the invention. The immune disorder includes allergy, autoimmunity, inflammatory bowel diseases, systemic autoimmune conditions, dysregulation of cell proliferation and apoptosis and immunopathological conditions of the skin, the oral cavity, the gastrointestinal, urogenital or respiratory tracts. Also, the disorders may be associated with prematurity and/or low birth weight and the composition administered to a child in need of such treatment.

BRIEF DESCRIPTION OF THE DRAWINGS

FIG. 6 illustrates the protein encoded by the OPG plasmid inserted in *Y. Lipolytica* (SEQ ID NO.: 6), wherein the OPG is indicated in bold print; and FIGS. 7A and 7B illustrates the sequence of milk OPG (SEQ ID NO: 1—amino sequence; SEQ ID NO: 7—nucleotide sequence).

DETAILED DESCRIPTION OF THE PREFERRED EMBODIMENTS

Figure 1:
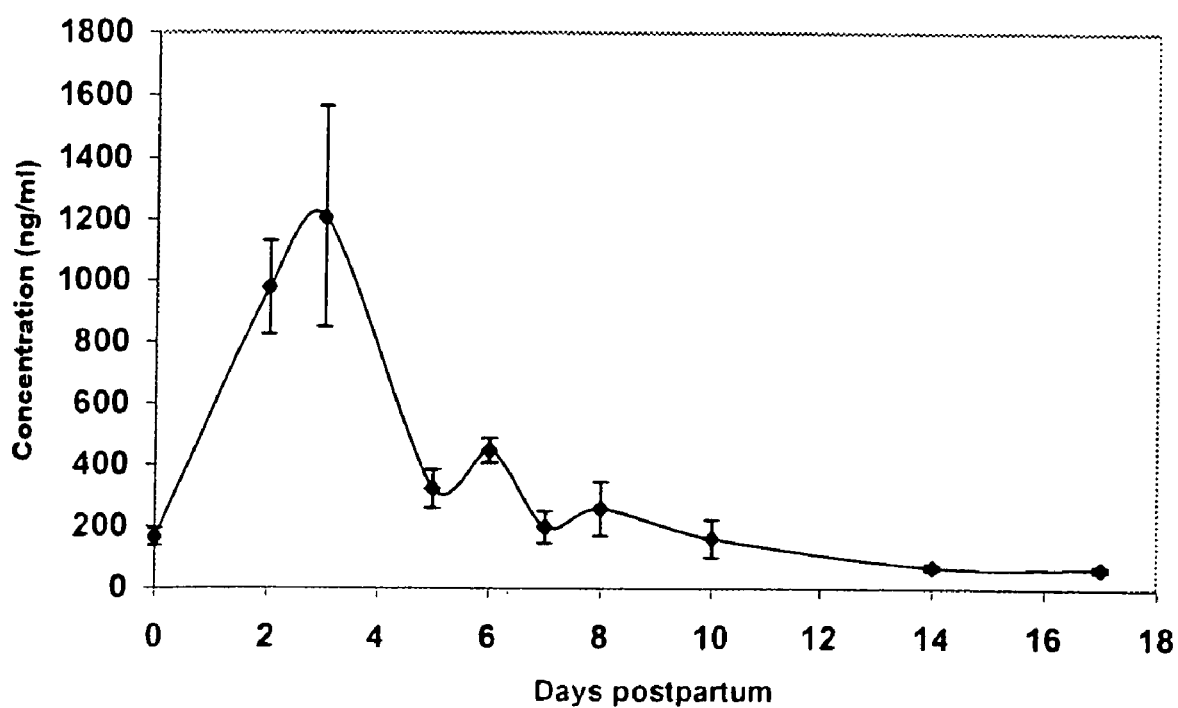
FIG. 1 shows the concentration of osteoprotegerin in human breast milk during various stages of lactation.
Figure 2:
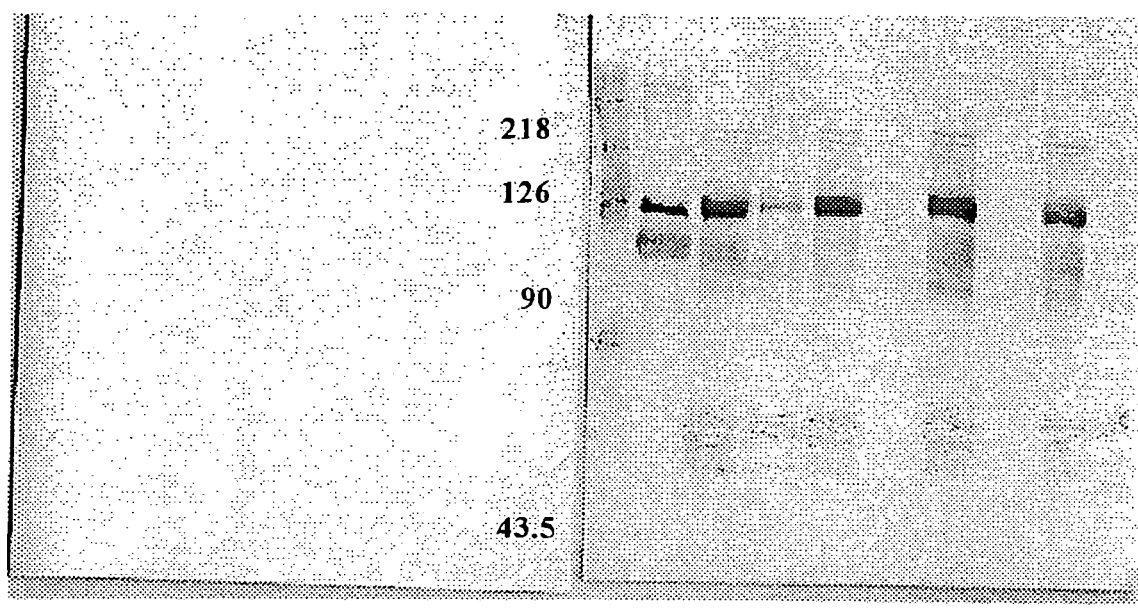
FIG. 2 shows a Western blot analysis of human milk fractions under reducing conditions using 10% SDS-gel. Bands for OPG were revealed using the biotinylated anti-OPG polyclonal antibody, BAF805 from R&D Systems and streptavidin-alkaline phosphatase (SAPP)

Osteoprotegerin (OPG), also known as osteoclastogenesis inhibitory factor (OCIF) and TNF-receptor-like molecule 1 (TR1), is a recently described member of the tumor necrosis factor family of receptors (TNFR). It inhibits osteoclast development both in vitro and in vivo and increases bone density (osteoperosis). In normal mouse embryos, OPG has been localized within cartilage rudiments of developing bones, as well as in the small intestine.

However, unlike other members of the TNF receptor family, OPG does not possess a transmembrane domain. Moreover, it could be shown that OPG is also a receptor for the cytotoxic ligand TRAIL (TNF-related apoptosis-inducing ligand) and is identical to follicular dendritic cell-derived receptor-1. As such, it is presumed to regulate cell death, as well as play an important role in the formation of lymphoid tissues and the regulation of immune responses. Indeed, animals lacking OPG have been shown to exhibit underdeveloped lymphoid tissues.

In the studies leading to the present invention, it has now surprisingly been found that in addition to its presence in e.g. the bone tissues, osteoprotegerin may also be found in human breast milk. In consequence, during breast feeding the mother is obviously supplying the newborn with this bioactive substance in a form that is capable of surviving in the child's gastro-intestinal tract. From this it follows that the OPG produced by mammary gland cells obviously differs from OPG isolated from other sources as regards its stability and/or resistance to degradation.

Without wishing to be bound by theory, it is presently believed that the specific glycosylation pattern conveyed to the protein in mammary gland cells renders the polypeptide more stable vis-a-vis the acidic gastric fluid and/or the basic environment encountered in the intestine, so that upon intestinal absorption and transport to the bone tissue, the active domain remains intact and is capable of exerting its biological activity.

The OPG of the present invention, i.e. in a form obtainable from milk source, has a polypeptide sequence as identified by SEQ ID. No. 1 and exhibits sizes of about 80, 130 and 200 kDa, respectively, which differs from that obtained by recombinant means (i.e., 55 kDa).

The OPG of the present invention may be included in an ingestable preparation, which may be a food material, such as e.g. milk, yogurt, curd, cheese, fermented milks, milk-based fermented products, ice-creams, fermented cereal-based products, milk-based powders, infant formulae and also pet food. Likewise, the OPG of the present invention may also be included in a enteral or pharmaceutical composition e.g. selected from the group consisting of solutions, dried oral supplement, liquid oral supplement, dry tube feeding or liquid tube-feeding.

In fact, since the OPG according to the present invention is stable, there is no need to bring the active compound into a specific galenic form so as to protect it from the differing and potentially detrimental conditions prevailing in the gastrointestinal tract and body fluids.

According to another aspect the present invention also provides for the use of osteoprotegerin from milk for preparing an ingestable preparation, such as a food material or an enteral composition, or a pharmaceutical composition.

The osteoprotegerin of the present invention and the ingestable preparation as detailed above may be used for the treatment and/or prophylaxis of disorders of bone remodeling.

The most common bone disorder is osteopenia, a condition relating in general to any decrease in bone mass to below normal levels. Such a condition may arise from a decrease in the rate of bone synthesis or an increase in the rate of bone destruction or both. The most common form of osteopenia is primary osteoporosis, also referred to as postmenopausal and senile osteoporosis. This form of osteoporosis is a consequence of an universal loss of bone with age and is usually a result of increase in bone resorption with a normal rate of bone formation. Yet other forms of osteoporosis include endocrine osteoporosis (hyperthyroidism, hyperparathyroidism, Cushing's syndrome, and acromegaly), hereditary and congenital forms of osteoporosis (osteogenesis imperfecta, homocystinuria, Menkes' syndrome, and Riley-Day syndrome) and osteoporosis due to immobilization of extremities.

Quite recently, it has been acknowledged that osteoporosis in human populations has also been associated with a higher incidence of arterial calcification, a component of many atherosclerotic lesions.

Consequently, a food product as illustrated above may well be utilized for preventing the onset of or alleviating symptoms and/or structural changes in the bones associated with osteopenia or osteoporosis, respectively. It will be appreciated that the active substance will be included in the food material in an amount sufficient to effect a desired biological response. Since OPG has been found to be itself a constituent of mother's milk, milk-based products are inherently well suited for delivering the substance to an individual.

On the other hand, for treating severe cases of osteopenia or osteoporosis, respectively, the preferred regimen may be a pharmaceutical composition, which contains the osteoprotegerin according to the present invention in higher amounts, that is in amounts sufficient to stop or even revert the disease process. Such compositions may contain the OPG of the present invention as the only active substance. This has the advantage that no major formulation of the substance has to be envisaged. It is, therefore, well within the present invention to simply press a tablet consisting of "OPG-powder" optionally supplemented with carriers or flavoring agents. However, in the case that the OPG of the present invention shall be formulated together with other active substances, the nature and liability to degradation of these additional substances in the gastro-intestinal tract shall be considered. The OPG of the present invention formulated in dosage units, will enable the attending physician to more carefully control the daily or weekly dose of the active compound.

The osteoprotegerin of the present invention may also be utilized for preventing the onset of and/or treating Paget's disease of bone, osteomyelitis, infectious lesions in bone which lead to bone loss, hypercalcemia, osteonecrosis, bone loss due to osteoarthritis or rheumatoid arthritis, periodontal bone loss and/or osteolytic metastasis.

OPG has also been found to be a receptor for the tumor necrosis factor-related ligand (TRAIL) which induces apoptosis upon binding to its death domain-containing receptors. It is presumed to regulate cell death, as well as play an important role in the formation of lymphoid tissues and the regulation of immune responses. Furthermore, OPG is a decoy receptor for RANKL (ligand for the receptor activator of NF-xB) which has been reported as a product of activated T cells. Ligation of the receptor for RANKL on mature dendritic cells, enhances dendritic cell survival. Furthermore, the engagement of RANKL with its receptor enhances T-cell growth and dendritic cell function.

Accordingly, the present invention provides for the use of osteoprotegerin obtainable from human and/or bovine milk for the manufacture of an ingestable preparation, such as e.g. a dietary composition or an enteral composition, or for the manufacture of a medicament, respectively, for contributing to the normal development of immune tissues, for contributing to normal immune function and even for preventing and/or treating disorders of the immune system.

Disorders of the immune system contemplated in the present invention comprise allergy, autoimmunity, sepsis, cancer, inflammatory bowel diseases, systemic autoimmune conditions, cardiovascular disease and immunopathological conditions of the skin, the oral cavity, the gastrointestinal, urogenital or respiratory tracts.

In addition, the osteoprotegerin of the present invention may likewise by applied for the regulation of cell proliferation and apoptosis, for the promotion of oral tolerance, the modulation of infectious processes and bacterial colonization of the neonate. Especially for neonates the above mentioned disorders may by and large be associated with prematurity and/or low birth weight, so that in these cases the osteoprotegerin of the present invention may simply be administered to the baby by means of baby food.

It will be appreciated that an individual at any age may be the individual to be treated, though babies and elderly are the main subjects to be considered due to their inherent requirement of exogenous osteoprotegerin. In particular individuals, such as newborns, require osteoprotegerin for the development of bone material and/or the immune system, so that in these cases the compound and/or the food material and/or the pharmaceutical composition of the present invention may be advantageously be administered.

However, it will be appreciated that the present invention may also be applied to adults, in order to prevent the onset of any of the above disorders. It will also be appreciated that apart from humans the individuals to be treated may also be animals, such as pets, in that the OPG of the present invention is included in pet food.

The OPG of the present invention may be obtained from a milk source, derived from a mammal, in particular from human or bovine milk or colostrum. Human milk OPG has an amino acid sequence of 380 as and exhibits a molecular weight of approximately 80, 130 and 200 kda when compared to protein markers which were used as molecular weight standards (BioRad). It exhibits 4 sites for N-glycosylation and may be present in a monomeric form and a dimeric form by forming a S—S bond via $Cys^{379}$.

The OPG of the present invention may be isolated from milk sources, such as human or bovine milk. However, it will be appreciated that the present OPG may be prepared by recombinant means in appropriate cells yielding a glycoslyation pattern as found in the "milk-OPG". Preferred cells for expression are those of the mammary gland, since these cells may be expected to yield an identical or essentially identical glycosylation pattern.

Suitable cells for expressing the present OPG may be obtained by immortalization with appropriate means, such as the SV40 vector or the telomerase gene, and transformation with an expression vector containing a nucleotide sequence encoding the OPG polypeptide. The polypeptide of interest may be obtained by isolating it from the supernatant, in the event that the polypeptide is secreted, or by collecting the cells and isolating the polypeptide from the cells themselves. In the event of a continuous production, isolation from the supernatant will be preferred.

EXAMPLES

The following examples illustrate the invention without limiting it thereto.

Human Milk and Human Serum Samples

Human breast milk samples (10-60 ml) from healthy mothers were collected up to 17 days post-partum under sterile conditions by breast pump expression or occasionally by manual expression. The milk was expressed into sterile 50 ml centrifugation tubes and processed within 2 hrs of collection. Following centrifugation (200×g, 10 min), the cellular pellet was immediately removed and treated for RNA extraction. The remainder of the milk was frozen at −20° C. Human serum samples were obtained from healthy donors and kept at −20° C.

Fractionation of Human Breast Milk

Cream was extracted from whole milk by high speed centrifugation. The top cream layer was removed, washed in water and the cream washings were frozen at −20° C. until required. The separation of whey and casein was achieved by rennet enzyme treatment or chemical acidification (with HCl) of skimmed milk inducing casein clotting. Centrifugation of the treated milk then separates sweet whey from the non-soluble rennet casein and acid whey from acid casein respectively. Finally, soluble milk proteins (ultracentrifuged whey) and non soluble, micellar casein were prepared using ultracentrifugation. All casein and whey fractions were frozen at −20° C. until required.

Human Mammary Cell Line

MCF-7 (American Type Culture Center (ATCC), Manassas, Va., HTB-22), a human mammary cell line derived from the pleural effusion of a breast carcinoma, retains several characteristics of differentiated mammary epithelium. The cells were cultured in DMEM (Amimed Bioconcept, Allschwill, Switzerland) supplemented with 10% foetal calf serum (FCS, Amimed Bioconcept) and maintained at 37° C. in a humidified atmosphere containing 5% $CO_2$. The culture media was changed 2 to 3 times per week. Upon reaching confluency, cells were detached using trypsin/EDTA (Gibco-BRL) at 37° C. The cells were then prepared for RNA extraction.

Western blot analysis

Milk samples were diluted 1/25 with Laemmli reducing sample buffer and boiled for 5 min. The proteins were separated by 10% SDS-PAGE and transferred to nitrocellulose membranes (BioRad). The blots were probed with a biotinylated polyclonal anti-human OPG (BAF805 at 0.2 p.g/ml; R&D systems) and streptavidin-alkaline phosphatase (Pierce). Immunoreactivity was visualized with alkaline phosphatase substrate BCIP/NBT (Zymed Laboratories). Prestained protein markers were used as molecular weight standards (BioRad). Recombinant human OPG (R&D systems) was load at 25 ng/lane served as a positive control.

Expression of OPG by Human Breast Milk Cells and Human Mammary Gland Epithelial Cells Reverse transcription followed by PCR was used to amplify OPG transcripts in the total human breast milk cell population from a single mother at 18 days postpartum and in the human mammary gland epithelial cell line, MCF-7. Total RNA was extracted from the cells using the Trizol method (Gibco-BRL). Briefly, the Trizol (1 ml for 5-10×10$^6$ cells) was added to the cell pellet, pipetted up and down several times and transferred into an Eppendorf tube. Chloroform was added (0.2 ml for 1 ml Trizol), and the tubes were incubated for 5 min before centrifugation at 12,000×g for 15 min, 4° C. RNA was precipitated with an equal volume of isopropanol and centrifuged at 12,000×g for 10 min. Pellets were washed with 70% ethanol and then resuspended in sterile, deionized water. RNA was stored at −20° C. until required.

RNA samples were treated with RNase-free DNase I to eliminate contamination by genomic DNA. RNA was quantified by absorbance at 260 nm and 280 nm of an appropriate dilution (100-200 fold) in a spectrophotometer. The concentration of RNA (.tg/ml) was calculated as follow: Absorbance at $A_{260}$×dilution factor×40 mg/ml. A total RNA sample that is essentially free of proteins should have an A260/A280 ratio of 1.8-2.2.

RNA was reverse-transcribed with Moloney murine leukemia virus reverse transcriptase (Perkin-Elmer). RNA samples (0.5 µg of total RNA), 0.5 unit of RNase inhibitor, 1 mM of each dNTP, 0.5 nmol/ml of specific 3' primer, 5 mM $MgCl_2$ and 1.25 units of reverse transcriptase were incubated in a total volume of 10 µl of reaction mixture containing the enzyme buffer supplied by the manufacturer. The reaction mixture was incubated for 30 min at 42° C., and then heated for 5 min at 95° C. The reverse-transcripted products were then amplified with Gold DNA polymerase (Perkin Elmer) on a thermocycler (Biolabo, Scientific Instruments, Chatel St Denis, Switzerland). The polymerase chain reaction (PCR) was performed in a total volume of 50 1.11 using 10 µl of the reverse transcripted products in PCR buffer, 2 mM $MgCl_2$, 5 µM of each dNTP, 0.2 nmol/ml of both OPG-specific antisense

ACTAGTTATAAGCAGCTTATTTTTACTG, (SEQ ID NO:2)

and sense

GGAGGCATTCTTCAGGTTTGCTG (SEQ ID NO:3)

primers and 1.25 units of DNA polymerase. After an initial denaturation step of 10 min at 95° C., samples were amplified by 35 cycles of denaturation at 94° C. for 45 sec, annealing at 60° C. for 1 min, and extension at 72° C. of 1 min 30 sec, followed by a 7-min extension step at 72° C. All samples were subjected to RT-PCR with 13-actin as a positive control. Samples of RT-PCR products were loaded onto a 1.2% agarose gels (containing ethidium bromide) in 1×TAE buffer and separated by electophoresis at 150 V for 1 hr. RT-PCR products were visualised under UV light. The correct size of the bands was determined by comparison with DNA size markers (Boehringer Mannheim).

ELISA for Human OPG-(Sandwich Enzyme Immunoassay)

The concentration of OPG present in breast milk and different milk fractions was measured by ELISA. To this end, monoclonal antibodies against OPG (MAB805, 1 µg/ml; R&D Systems, UK) were coated onto 96-well plates (Nunc) by overnight incubation at 4° C. Plates were then washed twice with 0.05% Tween-20 in PBS. Non-specific binding was blocked by incubating the plates with 2% bovine serum albumin (BSA) in PBS for additional 2 hrs at room temperature. Samples or standard concentrations of recombinant OPG (0.119 to 121.5 ng/ml; R&D Systems) were incubated in PBS-BSA for 3 hrs at room temperature. Plates were then washed four times with PBS-Tween before addition of biotin-labelled anti-human 0 PG polyclonal antibody (BAF805, 0.5 µg/ml; R&D Systems) for another hour at room temperature. After an additional four washes, streptavidin-peroxidase (SAAP, 0.5 µg/ml. Kirkegaard % Perry KPL) was added for 1 hr at room temperature. Plates were then washed four times, and the substrate TMB peroxidase (KPL) was added. Plates were covered and incubated in the dark for five minutes. The enzymatic reaction was terminated by the addition of IN HCl.

Absorbance was read at 450 nm in an ELISA reader (Dynex Technologies). The detection limit was approximately 30 pg/ml.

Biological Activity of Human Milk OPG

OPG is a receptor for the tumour necrosis factor-related ligand (TRAIL) which induces apoptosis upon binding to its death domain-containing receptors, DR4 and DR5. A bioassay was developed in which human breast milk OPG could be tested for its ability to block the TRAIL-induced apoptosis of these cells.

Figure 5:
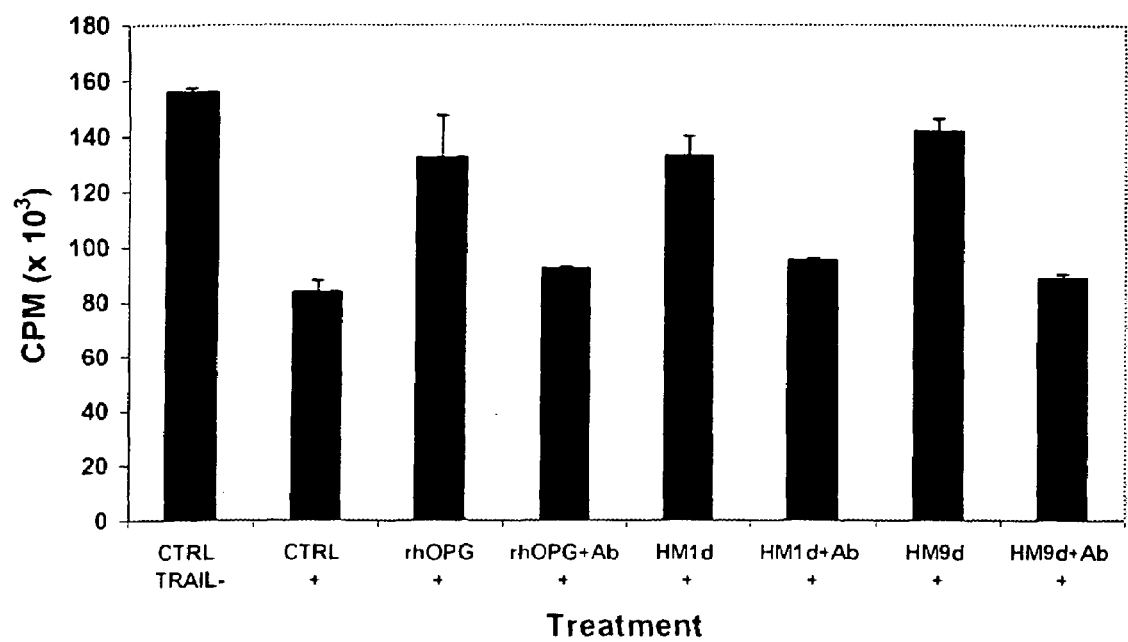
FIG. 5 shows the results of an experiment, wherein the OPG of the present invention inhibits TRAIL-induced apoptosis of Jurkat cells.

OPG inhibits TRAIL-induced apoptosis of Jurkat cells. FIG. 5 depicts a single representative experiment of Jurkat cells treated with 20 ng/ml of TRAIL and recombinant human OPG (rhOPG) or human milk (HM) at a final dilution of 1/80. The HM in the above experiment was from a single mother at either 1 day or 9 days postpartum. Antibody (Ab) against OPG was used at a concentration of 20 µg/ml. Cell proliferation was measured by $^3$H-thymidine incorporation. In control wells (CTRL), cells were exposed to culture medium with or without TRAIL.

In this respect Jurkat cells, clone E6-1 (ATCC), were maintained in culture in RPMI 1640 as modified by the supplier ATCC and containing 10% FCS (37° C. and 5% $CO_2$). Cells were seeded at a density of $5 \times 10^4$ cells/well in 96-well plates (Nunc). To each well various concentrations of soluble recombinant human TRAIL (0 to 20 ng/ml) were added in the presence of 2 µg/ml of enhancer protein, an antibody which reacts with soluble recombinant human TRAIL and thereby increases its activity (Alexis, Laufelfingen, CH). Some wells also contained 50 ng/ml recombinant human OPG (R&D Systems), human breast milk samples (HM; 1/80 final dilution; collected at 1d or 9d postpartum) and/or 20 gg/ml anti-OPG monoclonal antibody (MAB805, R&D Systems). Plates were incubated at 37° C. for 16 hrs.

Cell viability was measured by adding $^3$H-thymidine (1 µCi/well) during the last 6 hrs of culture.

In the medium control, a TRAIL-induced inhibition of cell proliferation was evident at concentrations greater than 5 ng/ml. However, HM samples prevented this inhibition. This effect was obviously due to the presence of OPG, since the at-OPG monoclonal antibody reversed the effect.

The results are shown in FIG. 5.

Western Blot Analysis

OPG is synthesized as a 55 kDa monomer within cells but is converted to a disulphide-linked dimer of approximately 110 kDa when secreted extracellularly. In milk bands were detected at approximately 80, 130 and 200 kDa.

Concentrations of OPG in Human Breast Milk

Levels of OPG in the breast milk samples of 10 lactating mothers at different times during the first 17 days of lactation were examined by ELISA. Concentrations increased to maximum values during the first 1-3 days of lactation and then decreased thereafter. Concentrations in milk ranged from 50 ng/ml to almost 2 µg/ml (FIG. 1).

Cellular Source of Milk OPG

Figure 4:
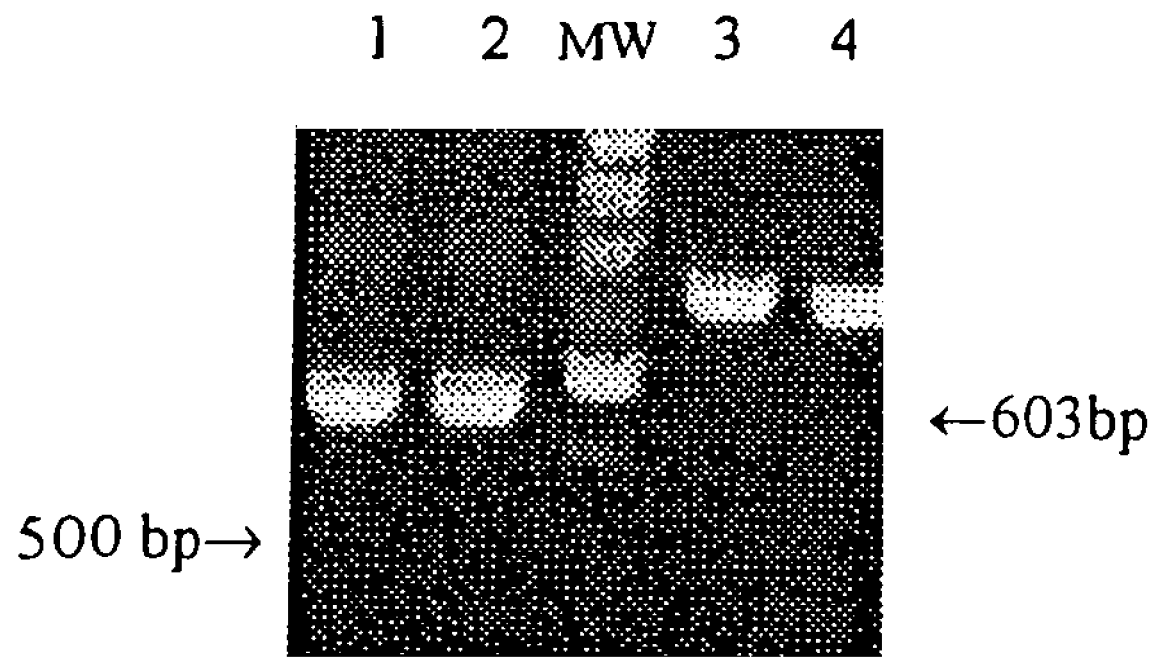
FIG. 4 shows a RT-PCR analysis of human breast milk cells and human mammary gland epithelial cells, MCF-7; Lanes 1 and 2:β-actin (expected size band: 460 bp); Lanes 3 and 4: OPG (expected size band: 603 bp); 1. Human breast milk cells; 2. MCF-7; 3. Human breast milk cells; 4. MCF-7.

RT-PCR analysis revealed that the OPG of the present invention may be found in human breast milk cells and mammary gland epithelial cells. Constitutive expression of mRNA for OPG was evident in both types of untreated cells (FIG. 4).

Cloning of Human Milk OPG in Yeast

Cells were isolated from human breast milk (18 days postpartum) by centrifugation (200×g, 10 min). From the cell pellet, total RNA was extracted using TRIzole (Life Technologies, Basel, Switzerland), DNAseI treated and further purified on RNeasy spin columns (Qiagen, Basel) as recommended by the manufacturers. A PCR product encoding the mature form of OPG was amplified from this total RNA using the Titan™One tube RT-PCR system following the protocol supplied by the manufacturer (Roche Diagnostics, Rotkreuz).

With the OPG specific antisense primer

```
CCGGCCTCTTCGGCCGCCAAGCGAGAAACGTTTCCTCCAAAGTACC,    (SEQ ID NO:4)
and the sense primer

Figure 3:
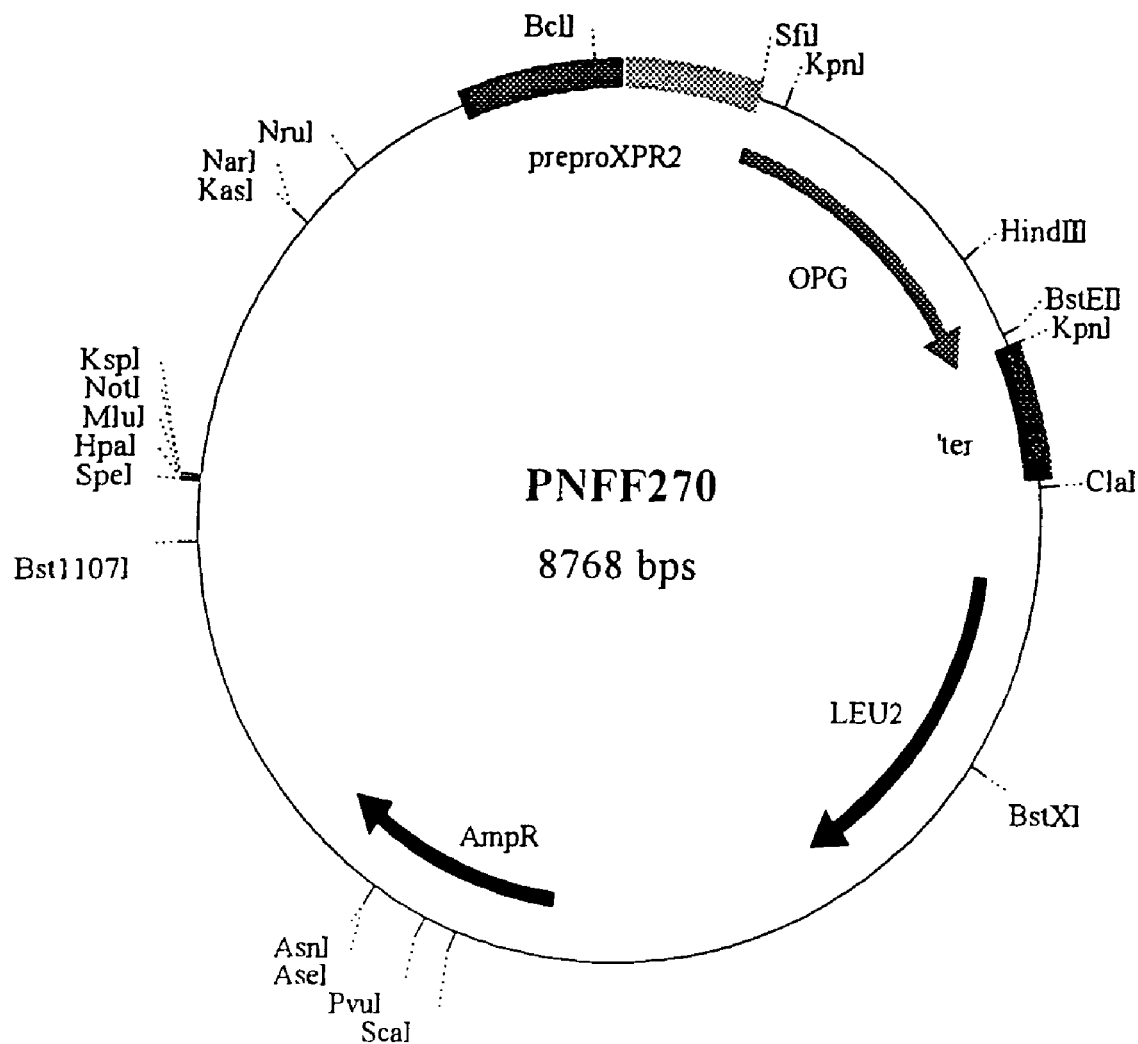
FIG. 3 shows the restriction map of the plasmid which was integrated into the genomic DNA of *Yarrowia* transformants.

ACTAGTTATAAGCAGCTTATTTTTACTG,                      (SEQ ID NO:5)
``` a 1174 bp PCR fragment was amplified from this cDNA. The PCR product was SfiI-SpeI digested, gel purified and the resulting 1156 bp fragment ligated to SfiI XbaI digested and SAP-treated pINA1267, creating pNFF270. This plasmid pNFF270 was then introduced into the yeast *Yarrowia lipolytica* by transformation. FIG. 3 depicts the restriction map of the plasmid which was integrated into the genomic DNA of *Yarrowia* transformants and SEQ ID. No. 1 the protein encoded by this OPG plasmid.

The sequence of a pGEM-T OPG clone is shown in FIG. 6. The mature OPG is in black and translated. In the published OPG/OCIF sequence, amino acid residue 242 of the mature OPG is an Ala-residue (A), whereas all pGEM-T OPG clones analyzed, encoded an Asp-residue (D) at this position. The SfiI-SpeI OPG fragment of this clone was transferred to SfiI-XbaI digested pINA1267. The resulting plasmid had the restriction map depicted in FIG. 3. A single copy of this plasmid was integrated into the genomic DNA of *Yarrowia* transformats. The protein encoded by this plasmid is shown in FIG. 4. The mature OPG is indicated in b old print. The plasmid p NFF270 w as introduced into *Yarrowia lipolytica* by transformation. The resulting transformants secreted a protein, cross-reacting with OPG-specific antibodies into the culture medium while *Y. lipolytica* transformants carrying the empty expression vector did not secrete such a protein.

What is claimed is:

1. A method for the treatment of disorders associated with bone remodeling which comprises administering to a person in need of such treatment an effective amount for the treatment or prophylaxis of a disorder associated with bone remodeling, of an ingestible composition of osteoprotegerin obtainable from bovine milk or colostrum, wherein the osteoprotegerin has a glycosylation pattern giving rise to a polypeptide having a molecular weight of approximately 130 kDa, and wherein the ingestible composition includes a food material selected from the group consisting of milk, yogurt, curd, cheese, fermented milks, milk-based fermented products, ice-creams, fermented cereal-based products, milk-based powders, infant formulae, pet food and combinations thereof.

2. The method according to claim 1, wherein the ingestible composition includes an enteral composition or a pharmaceutical composition containing osteoprotegerin in an amount effective to assist in treatment of disorders associated with bone remodeling in a subject that consumes the composition.

3. The method according to claim 2, wherein the enteral or pharmaceutical composition is selected from the group consisting of a solution, dried oral supplement, liquid oral supplement, dry tube-feeding and liquid tube-feeding.

4. The method according to claim 1, wherein the disorders include osteoporosis, Paget's disease of bone, osteomyelitis, infectious lesions in bone leading to bone loss, hypercalcemia, osteopenia, osteonecrosis, bone loss due to osteoarthritis or rheumatoid arthritis, periodontal bone loss and osteolytic metastasis.

* * * * *